(12) United States Patent
Houston

(10) Patent No.: US 6,808,708 B2
(45) Date of Patent: Oct. 26, 2004

(54) COMPOSITIONS AND METHODS RELATING TO REDUCTION OF SYMPTOMS OF AUTISM

(75) Inventor: Devin B. Houston, Forsyth, MO (US)

(73) Assignee: ProThera, Inc., Pleasanton, CA (US)

( * ) Notice: Subject to any disclaimer, the term of this patent is extended or adjusted under 35 U.S.C. 154(b) by 199 days.

(21) Appl. No.: 10/237,160

(22) Filed: Sep. 5, 2002

(65) Prior Publication Data

US 2003/0133926 A1 Jul. 17, 2003

Related U.S. Application Data

(63) Continuation of application No. 09/411,605, filed on Oct. 1, 1999, now Pat. No. 6,447,772.

(51) Int. Cl.[7] .......................... A61K 38/48; C12N 9/48; C12N 9/62
(52) U.S. Cl. ..................... 424/94.63; 435/212; 435/225
(58) Field of Search ...................... 424/94.63; 435/212, 435/225

(56) References Cited

U.S. PATENT DOCUMENTS

| | | | |
|---|---|---|---|
| 5,084,007 A | 1/1992 | Malin et al. ................... | 604/20 |
| 5,491,169 A | 2/1996 | Roques et al. .............. | 514/529 |
| 5,816,259 A | 10/1998 | Rose .......................... | 128/898 |
| 6,251,391 B1 | 6/2001 | Wilkinson et al. ........ | 424/94.63 |
| 6,329,336 B1 * | 12/2001 | Bridon et al. ................... | 514/2 |
| 6,447,772 B1 | 9/2002 | Houston ................... | 424/94.63 |
| 2002/0041871 A1 * | 4/2002 | Brudnak ................... | 424/94.65 |

OTHER PUBLICATIONS

"The Safety of Enzymes Derived from Aspergillus" *National Enzyme Company*, 1997.
Ackerman, L., "*Discussion of Autism General Information*" (1997).
Cade, Robert et al., "Autism and Schizophrenia: Intestinal Disorders" Abstract, Departments of Medicine, Physiology and Psychology, University of Florida, (1997).
Chich, Jean–Francois. 136. X–Pro dipeptidyl–peptidase. *Handbook of Proteoytic Enzymes*, Academic Press, pp. 1–3 (1998).
Chabance, B., et al., "Casein Peptide Release And Passage To The Blood In Humans During Digestion Of Milk Or Yogurt," *Biochimie* 80:155–165 (1998).
Fukudome, S. et al., "Opioid Peptides Derived From Wheat Gluten: Their Isolation And Characterization," *F.E.B.S.*, 296(1):107–111 (1992).
Kitozono, Ana et al. 139. Prolyl aminopeptidase. *Handbook of Proteoytic Enzymes*, pp. 412–413, (1998).
Kozakova, H., et al., "Brush Border Enzyme Activities In The Small Intestine After Long–Term Gliadin Feeding In Animal Models Of Human Coeliac Disease," *Folia Microbiol. (Praha)* 43(5):497–500 (1998) (Abstract).
Kreil, G., et al., "Studies On The Enzymatic Degradation Of Beta–Casomorphins," *Life Sci.* 33 Suppl 1:137–40 (1983) (Abstract).
Krepela E., et al., "Demonstration Of Two Molecular Forms Of Dipeptidyl Peptidase IV In Normal Human Serum," *Physiol. Bohemosloy* 32(6):486–96 (1983) (Abstract).
McDonald, J. Ken. 138. Dipeptidyl–peptidase II. *Handbook of Proteoytic Enzymes*, pp. 408–411, (1998).
*The Merck Manual of Medical Information*, Robert Berkow, et al., eds "Seizure Disorders," pp. 376–381, (1997).
*The Merck Manual of Medical Information*, Robert Berkow, et al., eds., "Childhood Schizophrenia," pp. 1436–1437, (1997).
*The Merck Manual of Medical Information*, Robert Berkow, et al., eds., "Schizophrenia and Delusional Disorder," pp. 475–479, (1997).
*The Merck Manual of Medical Information*, Robert Berkow, et al., eds., "Attention Deficit Disorder," pp. 1365–1367, (1997).
*The Merck Manual of Medical Information*, Robert Berkow, et al. eds., "Autism," pp. 1434–1435, (1997).
Misumi, Yoshio and Ikehara, Yukio. 129. Dipeptidyl–peptidases A and B. *Handbook of Proteoytic Enzymes*, pp. 382–383, (1998).
Reichelt, L. Karl, et al., "Nature And Consequences Of Hyperpeptiduria And Bovine Casomorphins Found In Autistic Syndromes," *Brain Dysfunct* 7:71–85 (1994).
Reichelt, L., Karl, et al., "Probable Etiology and Possible Treatment of Childhood Autism," *Brain Dysfunct* 4:308–319 (1991).
Reichelt, L. Karl, et al., "Gluten, Milk Proteins And Autism: Dietary Intervention Effects On Behavior And Peptide Secretion," *J Applied Nutrition* 42(1):1–11 (1990).
Seroussi, K., "Frequently Asked Questions about Dietary Intervention for the Treatment of Autism" (1995), www.en-abling_org/ia/celiac/aut/autgffaq.html.
Sjostrom, H. et al., "Intestinal Peptidases And Sucrase In Celiac Disease," *Clin. Chim. Acta*, 109(1):53–8 (1981) (Abstract).

(List continued on next page.)

Primary Examiner—Ponnathapura Achutamurthy
Assistant Examiner—William W. Moore
(74) Attorney, Agent, or Firm—Graybeal Jackson Haley LLP

(57) ABSTRACT

Methods and compositions that can reduce the symptoms of autism in a human patient comprising administering a physiologically effective amount of one or both of a purified casomorphin inhibitor selected from the group consisting of a casomorphinase and a casomorphin ligand, and a physiologically effective amount of a purified gluteomorphin inhibitor selected from the group consisting of a gluteomorphinase and a gluteomorphin ligand, to a human patient in sufficient quantities to reduce the effects of the autism. In some embodiments, the compositions and methods further comprise a physiologically effective amount of an enkephalin inhibitor, preferably an enkephalinase, and a physiologically effective amount of an endorphin inhibitor, preferably an endorphinase.

4 Claims, 1 Drawing Sheet

OTHER PUBLICATIONS

Sun, Z., et al., "A Peptide Found In Schizophrenia And Autism Causes Behavioral Changes In Rats," *Autism* 3(1):85–95 (1999).

Sun, Z., et al., "B–casomorphin induces Fos–like immunoreactivity in discrete brain regions relevant to schizophrenia and autism" *Autism* 3(1) 67–83, (1999).

Takahashi, K., "The Specificity Of Peptide Bond Cleavage Of Acid Proteinase A From Aspergillus Niger Var. Macrosporus Toward Oxidized Ribonuclease A," *Biosci. Biotech. Biochem*, 61(2):381–383 (1997).

Takahashi, K., et al., "Structure and Function of Pepstatin–Insensitive Acid Proteinase From *Aspergillus niger* var. *Macrosporus*" *Structure and Function of the Aspartic Proteinases*, B.M. Dunn, ed., Plenum Press, New York, pp. 203–211, (1991).

Whitely, P., et al., "A gluten–free diet as an intervention for autism and associated spectrum disorders: preliminary findings," *Autism* 3(1) 45–65, (1999).

Wilk, Sherwin, 525. Pro–X dipeptidase. *Handbook of Proteoytic Enzymes*, p. 1517, (1998).

* cited by examiner

SEQUENCE LISTING (1) GENERAL INFORMATION:

(iii) NUMBER OF SEQUENCES: 5

(2) INFORMATION FOR SEQ ID NO: 1:

(i) SEQUENCE CHARACTERISTICS:
       (A) LENGTH: 4 amino acids
       (B) TYPE: amino acid
       (C) STRANDEDNESS: single
       (D) TOPOLOGY: linear (ii) MOLECULE TYPE: peptide (iii) HYPOTHETICAL: NO (v) FRAGMENT TYPE: N-terminal (xi) SEQUENCE DESCRIPTION: SEQ ID NO: 1:

Tyr Pro Phe Pro
1

(2) INFORMATION FOR SEQ ID NO: 2:

(i) SEQUENCE CHARACTERISTICS:
       (A) LENGTH: 5 amino acids
       (B) TYPE: amino acid
       (C) STRANDEDNESS: single
       (D) TOPOLOGY: linear (ii) MOLECULE TYPE: peptide (iii) HYPOTHETICAL: NO (v) FRAGMENT TYPE: N-terminal (xi) SEQUENCE DESCRIPTION: SEQ ID NO: 2:

Gly Tyr Tyr Pro Thr
1           5

(2) INFORMATION FOR SEQ ID NO: 3:

(i) SEQUENCE CHARACTERISTICS:
       (A) LENGTH: 4 amino acids
       (B) TYPE: amino acid
       (C) STRANDEDNESS: single
       (D) TOPOLOGY: linear (ii) MOLECULE TYPE: peptide (iii) HYPOTHETICAL: NO (v) FRAGMENT TYPE: N-terminal (xi) SEQUENCE DESCRIPTION: SEQ ID NO: 3:

Gly Phe Phe Pro
1

(2) INFORMATION FOR SEQ ID NO: 4:

(i) SEQUENCE CHARACTERISTICS:
       (A) LENGTH: 5 amino acids
       (B) TYPE: amino acid
       (C) STRANDEDNESS: single
       (D) TOPOLOGY: linear (ii) MOLECULE TYPE: peptide (iii) HYPOTHETICAL: NO

```
        (v) FRAGMENT TYPE: N-terminal (xi) SEQUENCE DESCRIPTION: SEQ ID NO: 4:

Phe Gly Gly Tyr Leu
1               5

(2) INFORMATION FOR SEQ ID NO: 5:

(i) SEQUENCE CHARACTERISTICS:
            (A) LENGTH: 4 amino acids
            (B) TYPE: amino acid
            (C) STRANDEDNESS: single
            (D) TOPOLOGY: linear (ii) MOLECULE TYPE: peptide (iii) HYPOTHETICAL: NO (v) FRAGMENT TYPE: N-terminal (xi) SEQUENCE DESCRIPTION: SEQ ID NO: 5:

Phe Gly Gly Tyr
1
```

COMPOSITIONS AND METHODS RELATING TO REDUCTION OF SYMPTOMS OF AUTISM

RELATED APPLICATIONS

This application is a continuation application of U.S. patent application Ser. No. 09/411,605, filed Oct. 1, 1999, now U.S. Pat. No. 6,447,772, the contents of which are incorporated by reference in their entirety.

FIELD OF THE INVENTION

The field of the present invention is the reduction of symptoms of autism

BACKGROUND OF THE INVENTION

Autism is a relatively rare syndrome of early childhood that affects between three and eight of every 10,000 school-aged children. Autism is a serious disease that seriously impairs the functioning and life-enjoyment of its victims. The disease can include language disorders with impaired understanding, echolalia, pronominal reversal (such as using "you" instead of "I" or "me" when referring to one's self), rituals and compulsive phenomena, and uneven intellectual development with mental retardation. Autism is about two to five times more common in boys than in girls. The cause of autism is unknown, but there are, at the least, some important genetic factors, as indicated by the fact the concordance rate is significantly greater in monozygotic twins than dizygotic twins. Merck Manual, $17^{th}$ edition, section 19, chapter 274 (1999); Autism Review, Lowell Ackerman, http://www.parentzone.com/autism/review.htm (1997). Other factors may include rubella, problems during pregnancy, labor and delivery, cytomegalic inclusion disease, phenylketonuria, and fragile X syndrome. Autistic children are also at increased risk of developing seizure disorders, especially during their teen years.

Analysis of the urine of autistic children found hyperpeptiduria in the children, which means that the analysis found a significantly increased presence of peptides (short chains of amino acids) in the urine of children. Reichelt et al., *J. Applied Nutr.*, 42(1):1–11 (1990); Reichelt et al., *Brain Dysfunct.*, 4:308–319 (1991); Reichelt et al., *Dev. Brain Dysfunct,*. 7:71–85 (1994). Reichelt et al. (1994) hypothesized that the peptiduria was caused by insufficient breakdown of peptide fragments from dietary milk protein (i.e., casein) and wheat protein (i.e., gluten), resulting in the uptake of the peptides by the body. This is problematic because the peptides from casein and gluten, casomorphin and gluteomorphin, respectively, have opioid qualities, which means that they mimic opiates in the body (indeed, that is indicated by the "-morphin" suffix of the names, which shows their functional similarity to morphine, a strong opiate; casomorphin is also known as caseomorphine). For example, one molecule of gluten contains 15 opioid sequences, which can be released by the action of trypsin, chymotrypsin, and secretin. Id. Reichelt et al. also hypothesized that the release of the opioid-like casomorphin (from casein) and gluteomorphin (from gluten) were caused by a defect of peptidases in the patient. Reichelt et al. (1991) at 308.

Accordingly, Reichelt et al. proposed a strict gluten-free and casein-free diet (i.e., strictly wheat-free and dairy-free). Reichelt et al. (1990) found that such a diet ultimately resulted in increased social contact, decreased stereotypy, an end to self-mutilation like head banging, and a decrease in dreamy state periods. Also, alimentary problems generally improved. Reichelt et al. (1990) at 5; accord Reichelt et al. (1991); Reichelt et al. (1994).

Ackerman (1997) hypothesized that the addition of papain, bromelain, and chymotrypsin to the diet of the patient might be beneficial. However, Ackerman never reported the actual use of any such enzymes, and his proposed combination would not be expected to work because chymotrypsin, according to Reichelt et al. (1994) at 79, is one of the digestive enzymes believed to release the detrimental opioid sequences (as well as trypsin and the hormone secretin). Papain and bromelain are, likewise, broad-spectrum digestive enzymes that would also have a reasonably high chance of actually increasing the amount of opioids, i.e., casomorphins or gluteomorphins, instead of reducing them (absent the additional use of an agent to specifically inhibit the casomorphin or gluteomorphin, as discussed further herein).

As noted above, Reichelt et al. found that a strict gluten-free and casein-free diet had beneficial effects for the patient. However, as described by Seroussi, *Frequently Asked Questions About Dietary Intervention For The Treatment Of Autism And Other Developmental Disabilities*, http://www.enabling.org/ia/celiac/aut/autgfffaq.html (1999), achieving and maintaining such a diet can be very difficult: "Be careful. Removing all dairy means ALL milk, butter, cheese, cream cheese, sour cream, etc. It also includes product ingredients such as 'casein' and 'whey,' or words even containing the word 'casein.' Read labels—items like bread and tuna fish often contain milk products. Even soy cheese usually contains caseinate." Failure to adhere to the strict diet can be seriously detrimental: "What you need to understand is that for certain children, these [dairy and wheat] foods are toxic to their brains . . . You would never knowingly feed your child poison, but if he fits into this category, that is exactly what you could be doing." Id.; see Reichelt et al. (1991) (abstract; those patients that remained on the diet had further improvement, while those that abandoned the diet showed regression).

Thus, there has gone unmet a need for improved methods of treating patients with autism who exhibit the effects of exorphins such as gluteomorphin and casomorphin without requiring the patient to adhere to difficult dietary restrictions. Similarly, there has gone unmet a need to protect autistic patients from inadvertent exposure to gluten and casein, typically in the form of dairy products and wheat products. The present invention provides these and other advantages.

SUMMARY OF THE INVENTION

The present invention provides methods and compositions that can reduce the symptoms of autism in a human patient. Briefly, the methods and compositions comprise administering a physiologically effective amount of one or both of a purified casomorphin inhibitor selected from the group consisting of a casomorphinase and a casomorphin ligand, and a physiologically effective amount of a purified gluteomorphin inhibitor selected from the group consisting of a gluteomorphinase and a gluteomorphin ligand to a human patient in sufficient quantities to reduce the effects of the autism. When administered to human patients suffering from autism, without restriction on the normal diet of the patients, the compositions and methods reduced one or more symptoms of autism, such as increased eye contact, better enunciation and use of pronouns, less fatigue, singing a song for the first time with the melody and words together and the entire song understandable, playing with age appropriate friends for the first time, fewer tantrums, better sleep patterns, improved politeness and coordination, being more loving, acknowledging another individual's emotion, increased voice and word association, and, in one case, noticing that a calendar needed changing. In addition, the present invention provides compositions and methods that inhibit gluteomorphin and casomorphin, and other exorphins, from sources other than casein and gluten, which assists in the treatment of autism for persons that are already wheat-free and dairy-free, yet are still ingesting, or otherwise taking in, exorphins from other sources.

Thus, in one aspect the present invention provides compositions able to reduce the symptoms of autism in a human patient, comprising a physiologically effective amount of a purified casomorphin inhibitor selected from the group consisting of a casomorphinase and a casomorphin ligand, a physiologically effective amount of a purified gluteomorphin inhibitor selected from the group consisting of a gluteomorphinase and a gluteomorphin ligand, and at least one of the group consisting of a physiologically acceptable carrier, adjuvant, excipient, buffer and diluent. In a preferred embodiment, the casomorphinase is a proline protease, further preferably a protease comprising the dipeptidase activity of dipeptidyl peptidase IV. (The present invention comprises multiple aspects, features and embodiments; such multiple aspects, features and embodiments can be combined and permuted in any desired manner.)

In another embodiment, the compositions comprise the casomorphin ligand or the gluteomorphin ligand, or the gluteomorphinase is selected from the group consisting of a tyrosinase and a phenylalaninase. The composition can be suitable for oral administration, and in one preferred embodiment the casomorphin inhibitor and the gluteomorphin inhibitor are not enterically coated, although they can also be enterically coated if desired. Also preferably, the casomorphin inhibitor comprises a microbial proline peptidase and the gluteomorphin inhibitor comprises a microbial gluteomorphinase selected from the group consisting of a tyrosinase and a phenylalaninase. At least one of the group consisting of the physiologically acceptable carrier, adjuvant, excipient, buffer and diluent comprises a carbohydrate, for example maltodextrin, L-lysine and lactase.

In other embodiments, composition further comprises a physiologically effective amount of an enkephalin inhibitor, preferably an enkephalinase and a physiologically effective amount of an endorphin inhibitor, preferably an endorphinase.

In another aspect, the present invention provides methods of reducing the symptoms of autism in a human patient, comprising administering to the patient a composition comprising a physiologically effective amount of a purified casomorphin inhibitor selected from the group consisting of a casomorphinase and a casomorphin ligand, a physiologically effective amount of a purified gluteomorphin inhibitor selected from the group consisting of a gluteomorphinase and a gluteomorphin ligand, and at least one of the group consisting of a physiologically acceptable carrier, adjuvant, excipient, buffer and diluent.

In a further aspect, the present invention provides methods of manufacturing a medicament able to reduce the symptoms of autism in a human patient, comprising combining a physiologically effective amount of a purified casomorphin inhibitor selected from the group consisting of a casomorphinase and a casomorphin ligand, a physiologically effective amount of a purified gluteomorphin inhibitor selected from the group consisting of a gluteomorphinase and a gluteomorphin ligand, and at least one of the group consisting of a physiologically acceptable carrier, adjuvant, excipient, buffer and diluent In yet another aspect, the present invention provides compositions able to reduce the symptoms of autism in a human patient, comprising a physiologically effective amount of a purified casomorphin inhibitor, a physiologically effective amount of a purified gluteomorphin inhibitor, and at least one of the group consisting of a physiologically acceptable carrier, adjuvant, excipient, buffer and diluent, wherein the casomorphin inhibitor comprises a proline protease grown by a process selected from the group consisting of tray fermentation and deep-tank fermentation and purified by a process comprising alcohol precipitation and filtration, and wherein the gluteomorphin inhibitor comprises a tyrosinase purified by the process of grown by a process selected from the group consisting of tray fermentation and deep-tank fermentation and purified by a process comprising alcohol precipitation and filtration.

In still a further aspect, the present invention provides methods of reducing the symptoms of autism in a human patient, comprising administering to the patient a composition comprising a physiologically effective amount of a purified casomorphin inhibitor, a physiologically effective amount of a purified gluteomorphin inhibitor, and at least one of the group consisting of a physiologically acceptable carrier; adjuvant, excipient, buffer and diluent, wherein the casomorphin inhibitor comprises a proline protease purified by the process of grown by a process selected from the group consisting of tray fermentation and deep-tank fermentation and purified by a process comprising alcohol precipitation and filtration, and wherein the gluteomorphin inhibitor comprises a tyrosinase or a phenylalaninase purified by the process of grown by a process selected from the group consisting of tray fermentation and deep-tank fermentation and purified by a process comprising alcohol precipitation and filtration.

In yet still another aspect, the present invention provides compositions able to reduce the symptoms of autism in a human patient, comprising a means to inhibit casomorphin, a means to inhibit gluteomorphin, and at least one of the group consisting of a physiologically acceptable carrier, adjuvant, excipient, buffer and diluent.

In another aspect, the present invention provides methods of reducing the symptoms of autism in a human patient, comprising a step of administering to the patient a composition comprising a means to inhibit casomorphin, a means to inhibit gluteomorphin, and at least one of the group consisting of a physiologically acceptable carrier, adjuvant, excipient, buffer and diluent.

In still a further aspect, the present invention provides foods and food supplements comprising compositions as described herein.

In yet another aspect, the present invention provides kits comprising a vessel containing compositions as described herein and instructions directing the use of the composition to reduce autistic symptoms in a human patient of an exorphin selected from the group consisting of a gluteomorphin and a caseomorphin. In another embodiment, the present invention provides vessels containing such compositions and a label attached to the vessel comprising instructions directing the use of the composition to reduce the symptoms. These and other aspects, features and embodiments of the present invention will become evident upon reference to remainder of this application, including the following Detailed Description and attached drawings. In addition, various references are set forth herein that describe in more detail certain compositions, apparatus and/or methods; all such references are incorporated herein by reference in their entirety.

DETAILED DESCRIPTION OF THE INVENTION

Figure 1:
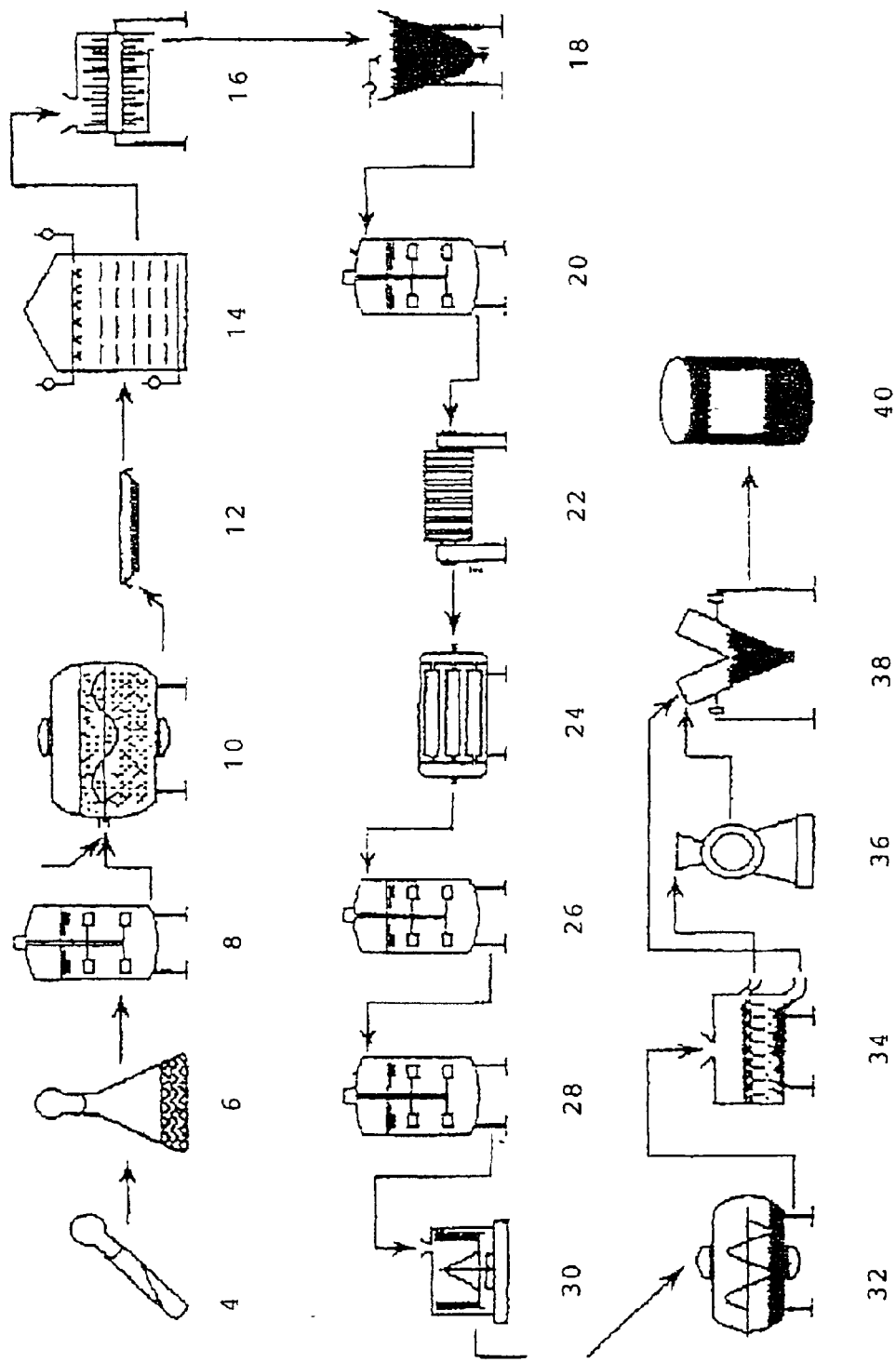
FIG. 1 depicts a method for the preparation of an exorphinase.

The present invention provides methods and compositions able to reduce the symptoms of autism in a patient, including a human patient. Briefly, the compositions and methods comprise administering a casomorphin inhibitor and/or gluteomorphin inhibitor to a human patient in sufficient quantities to reduce the effects of the autistic disease. An initial trial wherein casomorphin and gluteomorphin inhibitors were administered to human patients, without restriction on the normal diet of the patients, provided a significant number of the patients with a significant reduction of one or more symptoms, such as increased eye contact, better enunciation and use of pronouns, less fatigue, singing a song for the first time with the melody and words together and the entire song understandable, playing with age appropriate friends for the first time, fewer tantrums, better sleep patterns, improved politeness and coordination, being more loving, acknowledging another individual's emotion, increased voice and word association, and, in one case, noticing that a calendar needed changing.

The following paragraphs provide definitions of some of the terms used herein. All such terms, including those specifically described below in this section, are used in accordance with their ordinary meanings unless the context or definition indicates otherwise. Also unless indicated otherwise, except within the claims, the use of "or" includes "and" and vice-versa; similarly, non-limiting terms are not to be construed as limiting unless expressly stated (for example, "including" means "including without limitation").

"Composition" indicates a combination of multiple substances into an aggregate mixture.

A "purified" component of a composition, such as an exorphin inhibitor, indicates that the substance is more pure than when it occurs in its natural state, but it may potentially contain other enzymes and other active material. For example, a purified casomorphin inhibitor obtained from a cellular culture is more pure than when it was in existence in its originating cell, but may still contain other substances such as a gluteomorphin inhibitor, lactases, and other cellular material. "Highly purified" indicates that no other substances having significant biological activity, such as enzymatic activity, are present in the highly purified material (the highly purified material may have the presence of detectable but non-physiologically effective amounts of other activities).

A "physiologically effective amount" of an active substance such as an exorphin inhibitor indicates an adequate amount of the active substances to have a significant, externally observable effect on the patient. Thus, such a physiologically effective amount affects one or more of the characteristics in the patient without the need for special equipment to determine the effect. For example, a physiologically effective amount of an exorphin inhibitor has a significant, externally observable reduction of effect on the opioid-like bioactivity of the exorphin, and thus reduces one or more of the symptoms of autism in a human patient without the need for special equipment to determine the effect. Accordingly, one can determine whether an adequate amount of the active substance has been administered by watching the patient and observing whether changes have occurred in the patient due to the active substance.

"Protein" indicates an extremely complex combination of amino acids in a lengthy chain(s). Proteins are an essential constituent of living cells. "Proteases" are enzymes that act upon proteins to alter their structure or composition, for example by reducing them, oxidizing them or cleaving them into smaller chains of amino acids, typically without the enzymes themselves being consumed in the reaction.

"Peptide" indicates a small chain of amino acids, often derived from the breakdown of proteins. Peptides are typically comprised of two or more amino acids, but typically less than 10 or 20 amino acids. A "peptidase," like a protease, is an enzyme that acts on the peptide to alter the structure or composition of the peptide. An exopeptidase (like an exoprotease) acts on amino acids at the end of an amino acid chain, typically by cleaving them from the remainder of the chain. An endopeptidase (like an endoprotease) acts on amino acids within the middle of an amino acid chain. Thus, an exopeptidase can shorten an amino acid chain, while an endopeptidase can give multiple chains of amino acids from the initial substrate. A dipeptidase is a type of exopeptidase that cleaves at the penultimate position from the terminus of the peptide chain, thereby cleaving the peptide such that two amino acids are cleaved at one time from the remainder of the peptide.

"Exorphins" are external substances that have opiate-like (narcotic) activity in the body, thereby acting like the body's own narcotics, the endorphins. The two primary examples of exorphins relevant to the present application are casomorphins and gluteomorphins. By providing exorphin inhibitors, the present invention inhibits the opioid bioactivity of exorphins, by action of an exorphinase, which alters the structure or composition of the exorphins, for example by oxidation, reduction or cleavage, or by action of an exorphin ligand, which binds to the exorphin.

"Casomorphin" is an exorphin derived from casein via the activity of proteases, possibly including chymotrypsin and trypsin, as well as indirectly by the action of gastric hormones such as secretin. Casomorphins typically comprise the amino acid sequence Tyr-Pro-Phe-Pro (SEQ ID NO: 1).

A "casomorphin inhibitor" is a substance that inhibits the opioid-type bioactivity of casomorphin. The present invention is directed to two types of casomorphin inhibitors, casomorphinases and casomorphin ligands. A "casomorphinase" is an enzyme that inhibits the opioid-type bioactivity of casomorphin by altering the structure or composition of the casomorphin. For example, the casomorphinase may affect casomorphin by oxidation (the casomorphinase is an oxidase), reduction (a reductase) or cleavage (by action of a peptidase). A casomorphin ligand is a molecule that binds to the casomorphin such that the casomorphin substantially loses its opioid-type bioactivity.

"Gluteomorphin" is an exorphin derived from gluten via the activity of proteases, possibly including chymotrypsin and trypsin, as well as indirectly by the action of gastric hormones such as secretin. Gluteomorphins typically comprises an amino acid sequence of Gly-Tyr-Tyr-Pro-Thr (SEQ ID NO: 2), Gly-Phe-Phe-Pro (SEQ ID NO: 3), Phe-Gly-Gly-Tyr-Leu (SEQ ID NO: 4), or Phe-Gly-Gly-Tyr (SEQ ID NO: 5). According to Reichelt et al. (1991) one molecule of gluten contains about 15 different gluteomorphin, i.e., opioid, sequences.

A "gluteomorphin inhibitor" is a substance that inhibits the opioid-type bioactivity of gluteomorphin. The present invention is directed to two types of gluteomorphin inhibitors, gluteomorphinases and gluteomorphin ligands. A "gluteomorphinase" is an enzyme that inhibits the opioid-type bioactivity of gluteomorphin by altering the structure or composition of the gluteomorphin. For example, the gluteomorphinase may affect gluteomorphin by oxidation (the gluteomorphinase is an oxidase), reduction (a reductase) or cleavage (by action of a peptidase). A gluteomorphin ligand is a molecule that binds to the gluteomorphin such that the gluteomorphin substantially loses its opioid-type bioactivity.

A "proline protease" is a protease that cleaves a protein or a peptide on the basis of the presence of a proline amino acid in the sequence of the protein or peptide. "Dipeptidyl peptidase IV" ("DPP IV") is a Dipeptidyl peptidase that cleaves peptides comprising a proline at the penultimate position at the amino-terminus of the peptide. Handbook of Proteolytic Enzymes," CLAN SC-S9, § 128, p. 378–382 (Academic Press, Barrett, et al., eds., 1998). Similarly, a "tyrosinase" is a protease that cleaves, oxidizes and/or reduces a protein on the basis of a tyrosine in the protein. "Phenylalaninase" is an example of another exomorphinase, which cleaves, oxidizes and/or reduces a protein on the basis of a phenylalanine in the protein.

A "microbe" means microscopic organisms, including organisms such as bacteria and fungi.

"Enkephalin" indicates a naturally occurring substance in the brain, typically either of two penta-peptides, with opiate and analgesic activity and a marked affinity for opiate receptors. An enkephalin inhibitor is a substance that inhibits the bioactivity of an enkephalin such that the inhibition has an observable effect on a patient whose enkephalins have been so inhibited. An "enkephalinase" is an enzyme that oxidizes, reduces, cleaves or otherwise alters the structure or components of enkephalin such that it substantially loses its opiate activity. An "enkephalin ligand" is a substance that binds to the enkephalin such that the enkephalin substantially loses its opiate-type bioactivity.

An "endorphin" is any of a group of proteins with potent narcotic or analgesic properties that occur naturally in the brain. An endorphin inhibitor is a substance that inhibits the bioactivity of an endorphin such that the inhibition has an observable effect on a patient whose endorphins have been so inhibited. An "endorphinase" is an enzyme that oxidizes, reduces, cleaves or otherwise alters the structure and/or components of endorphin such that it substantially loses its opiate activity. An "endorphin ligand" is a substance that binds to the endorphin such that the endorphin substantially loses its opiate-type bioactivity.

The terms set forth in this application are not to be interpreted in the claims as indicating a "means plus function" relationship unless the word "means" is specifically recited in a claim, and are to be interpreted in the claims as indicating a "means plus function" relationship where the word "means" is specifically recited in a claim. Similarly, the terms set forth in this application are not to be interpreted in method or process claims as indicating a "step plus function" relationship unless the word "step" is specifically recited in the claims, and are to be interpreted in the claims as indicating a "step plus function" relationship where the word "step" is specifically recited in a claim.

Other terms and phrases in this application are defined in accordance with the above definitions, and in other portions of this application.

Turning to a more detailed discussion of the invention, in a first aspect the present invention provides compositions that are able to reduce the symptoms of autism in a human patient. For example, the compositions are able to reduce one or more symptoms, such as increased eye contact, better enunciation and use of pronouns, less fatigue, fewer tantrums, better sleep patterns, improved politeness and coordination, and increased voice and word association. In other words, the compositions are able to effect an adequate reduction of one or more of the observable characteristics of autism by an amount that is observable to a human observer, such as a parent, physician or caretaker, without the use of special devices such as microscopes or chemical analytical devices. The compositions reduce such symptoms by providing a physiologically effective amount of a purified casomorphin inhibitor selected from the group consisting of a casomorphinase and a casomorphin ligand and a physiologically effective amount of a purified gluteomorphin inhibitor selected from the group consisting of a gluteomorphinase and gluteomorphin ligand, and also at least one of the group consisting of a physiologically acceptable carrier, adjuvant, excipient, buffer and diluent, which terms are used in their ordinary sense to indicate substances that assist in the packaging, delivery, absorption, or, in the case of an adjuvant, enhancing the physiological effect of one or both of the casomorphin inhibitor and the gluteomorphin inhibitor.

The physiologically acceptable carriers, adjuvants, excipients, buffers and diluents are preferably nontoxic to recipients at the dosages and concentrations employed. Representative samples include water, isotonic saline solutions that are preferably buffered at physiological pH (such as phosphate-buffered saline or Tris-buffered saline), mannitol, dextrose, glycerol, and ethanol, as well as selected polypeptides or proteins such as human serum albumin, maltodextrin, L-lysine, lactase and other carbohydratases, lipase and non-specific proteases such as papain. The carrier, adjuvant, excipient, buffer, or diluent may be combined with the exorphin inhibitors to provide compositions either as liquid solutions or, preferably, in solid form. For example, when the compositions are to be administered orally, the compositions may be produced in any of powder, tablet or capsule form.

The compositions of the present invention are preferably administered orally, but may also be administered via other direct routes, such as rectal or, in the case of pharmaceutically designed compositions, via transcutaneous methods such as intraarterial, intramuscular, intraperitoneal, subcutaneous, intraocular, and intravenous. Other routes such as buccal/sublingual, nasal, topical (such as transdermal and hypothalamic), vaginal and pulmonary may also be used, if desired. The compositions are typically administered to human beings, but may also be administered to animals, preferably mammals, displaying symptoms similar to autism.

Turning to some of the other components of the compositions, the exorphin inhibitors, i.e., the casomorphin inhibitors and the gluteomorphin inhibitors, are present in the composition in adequate amounts to reduce one or more symptoms of autism in at least about one-fourth of the human patients to whom the composition is administered. Preferably, the composition reduces the symptoms of two or more symptoms of autism (or even up to 10 or more, or all), and further preferably reduces the symptoms in one-half or more of the human patients to which it is administered.

In a preferred embodiment, the casomorphin inhibitor is a casomorphinase, further preferably a proline protease, which means a protease that acts, typically by cleavage, on the substrate casomorphin based upon the presence of a proline amino acid residue within the peptide. Further preferably, the proline protease is a peptidase comprising a dipeptidase activity similar to that of DPP IV, which means that the protease cleaves at the penultimate position of a peptide when a proline is located at such penultimate position. Still further preferably, the proline protease is DPP IV.

In another embodiment, the gluteomorphin inhibitor is a gluteomorphinase, preferably a tyrosinase, which means an enzyme that oxidizes, reduces or cleaves the substrate gluteomorphin due to the presence of tyrosine residue(s) in the gluteomorphin. Rosei et al., *Recenti Prog. Med.*, ADH (3):134–139 (1997); Rosei et al, *Biochem. Int.*, 19(6): 1183–1193 (1989); Rosei et al., *Biochem. Biophys. Acta*, 1199(2):123–129 (1994); Larsimont et al., *Biochem. Biophys. Acta*, 1222(1):95–100 (1994). Further preferably, the tyrosinase comprises an oxidizing activity of the tyrosine when in the presence of L-dopa (L-dihydroxyphenylalanine) In a further embodiment, the gluteomorphinase is preferably a phenylalaninase, which means an enzyme that oxidizes, reduces or cleaves the substrate gluteomorphin due to the presence of phenylalanine residue(s) in the gluteomorphin.

As noted above, the compositions of the present invention can be administered orally to the patient. In a preferred embodiment, the casomorphin inhibitors and the gluteomorphin inhibitors of the present invention are not enterically coated, which means that the inhibitors have not been treated with any specific substances to assist the passage of the inhibitors through the rigors of the stomach to the intestines. Thus, in this embodiment, it is preferred to use exorphin inhibitors able to withstand such caustic stomach conditions. One example of suitable exorphin inhibitors are those derived from microbial sources such as bacteria and fungi. Preferred bacterial sources include members of the Bacillus, including *Bacillus amyloliquifaciens, Bacillus coagulans, Bacillus lichenformis, Bacillus macerans* and *Bacillus subtilis*. Preferred fungi include species of the genus Aspergillus, for example *Aspergillus oryzae, Aspergillus niger, Aspergillus awamori, Aspergillus flavus, Aspergillus japonicus, Aspergillus saitoi, Aspergillus sojae,* and *aspergillus usamii shirousami.*

In preferred embodiments, one or more, or all, of components of the composition are produced from a microbe such as the microbes discussed above or a recombinant microbe that has been produced by recombinant technology, or other methods of introducing foreign genes into a desired species or cell line. Thus, the recombinant microbe produces a desired agent for use in the compositions and methods of the present invention, such as a desired exomorphin inhibitor, enkephalinase or endorphinase. Preferred examples of such recombinant cell lines include *E. coli*, Sacchromyces, Candida, and desired mammalian or other eukaryotic cell lines. The microbes can be grown, for example, by the processes of solid state fermentation or deep-tank fermentation. In solid state fermentation, the microbes are typically grown on trays or other solid substrates, while in deep-tank fermentation the microbes re raised in large tanks using cultures submerged in a solution of oxygenated media.

In one embodiment, such fermentation comprises growing the enzyme-producing organism on a suitable energy-providing substrate such as koji (wheat or rice bran), which substrate has preferably been sterilized to eliminate unwanted organisms from the fermentation process. Thus, the sterile koji or other energy-providing material is inoculated with the desired strain of microbe that will produce the desired enzymes. Fermentation proceeds under controlled temperature and humidity conditions from about a few days to a week. At the conclusion of the fermentation, the enzymes are solubilized into an aqueous phase and substrate is removed by conventional filtration. If desired, microfiltration and/or ultrafiltration steps may also be used to concentrate the aqueous enzyme prior to precipitation. Where it is desired to produce powdered enzymes, soluble enzymes can be precipitated within an appropriate precipitating agent, for example an alcohol, preferably a non-toxic alcohol such as ethanol, then washed and dried. Pursuant to the precipitation step, the resulting powder product can be considered to be microbially very clean, which indicates that it has a very low level of microbes when compared to other products such as pasteurized (fluid) milk. In addition, the composition preferably is free of toxins, particularly mycotoxins in the case of fungi, which can be assayed using tests well known to those of ordinary skill in the art in view of the present disclosure. In addition, alternative methods of making and purifying desired enzymes and other exorphin inhibitors, from both microbial and non-microbial sources, and including alternative solid state fermentation processes, will be readily apparent to a person of ordinary skill in the art in view of the present specification. For example, the pH, temperature, buffers, sugars, minerals, and other parameters of the growth conditions can be adjusted as desired by a person having ordinary skill in the art in view of the present specification to enhance growth for particular desired substances, organisms or cell lines.

In additional embodiments, the compositions can further comprise one or both of an enkephalin inhibitor and an endorphin inhibitor. Such inhibitors function in much the same way as the exorphin inhibitors, and therefore the discussion herein relating to such inhibitors applies to the enkephalin and endorphin inhibitors as well.

In another aspect, the present invention provides compositions comprising microbially-derived casomorphinases in combination with a physiologically acceptable carrier, adjuvant, excipient, buffer or diluent. As noted above, in preferred embodiments the composition additionally comprises one or more of a gluteomorphin inhibitor, an enkephalin inhibitor and an endorphin inhibitor. Preferably, the inhibitors are not enterically coated.

In a preferred embodiment, the compositions are provided to the patient as either a food or a food supplement. For example, when provided as a food the compositions of the present invention are combined with material primarily made up of protein, carbohydrate and/or fat that is used in the body, preferably a human body, to sustain growth, repair, vital processes, and to furnish energy. When provided as a food supplement, the compositions comprise selected substances such that they can be eaten at or about the same time as a food. The food supplements are generally eaten within about one hour before or after the food is eaten, typically within about one-half hour before or after the food is eaten, preferably within about 15 minutes of when the food is eaten, and further preferably within one to five minutes of the time the food is eaten. The food supplement can also be eaten at the same time as, or even with the food.

In another aspect, the present invention provides methods for reducing the symptoms of autism in a patient, preferably a human patient. In one embodiment, such methods comprise administering compositions as described elsewhere herein to a patient in a physiologically effective amount to reduce one or more symptoms of autism, as described elsewhere herein.

In a preferred embodiment, as noted above, the methods comprise administering the compositions at or about the time that food containing, or potentially containing, casein or gluten are eaten by a patient, so that the exorphin-inhibitory activities of the composition will coincide with the presence of the food in the gut, preferably beginning in the stomach and continuing on into the intestines.

In an additional aspect, the present invention provides methods of manufacturing a medicament able to reduce the symptoms of autism wherein the medicament comprises the compositions as described elsewhere herein.

In an additional aspect, the present invention provides vessels comprising compositions as described herein and a label attached to the vessel wherein the label comprises instructions or directions advising a patient to use the composition to reduce the symptoms of autism. The vessel can be any appropriate container including a can, a vial, a box or any other appropriate vessel, for example such as a hypodermic needle for the intravenous administration of the composition. A label can be attached to the vessel via any suitable approach, including, for example, glue or a string. In a similar aspect, the present invention also provides kits comprising a vessel, as described above, and instructions. In the kit, the instructions need not be physically attached to the vessel.

EXAMPLES

Example 1
Production of Exorphinase from a Fungus.

As depicted in FIG. 1, an exorphinase was produced by first growing a desired microbe in a tube to provide a tube culture which was then expanded to a flask culture in a flask 6. The culture was then further expanded in a seed tank 8 and then introduced into a rotating cooker 10 containing wheat bran and water. The inoculate was then grown from two to ten days until a desired level of growth was attained, and then the inoculated wheat bran 12 was removed from the rotating cooker 10 and transferred to a cultivation chamber 14, which cultivation chamber was provided with water, steam and filtered air as desired.

The resulting cultured bran was then transmitted through a crusher 16 and then placed into an extractor 18 where it was extracted with water. The extract was placed into a first precipitation tank 20 comprising diatomaceous earth and ethanol, and the resulting solution was then transmitted through a filter press 22 where the resulting cake was discarded and the filtrate was transmitted on to a bacteriological filter 24. The filtrate from the bacteriological filter was then transmitted into a second precipitation tank 26 containing ethanol to provide a slurry. The slurry from the second precipitation tank 26 was then placed into a dehydration tank 28, also containing ethanol, and the resulting slurry was then centrifuged in a centrifuge 30. The resulting cake from the centrifuge was transferred to a vacuum dryer 32 where it was dried and then placed into a sifter 34. The material that sifted out was placed into a blender 38, while material too large to sift was run through a pulverizer 36 and then placed into the blender 38. In the blender, a desired diluent was added to provide a finished product contained in vessel 40.

Example 2
Exorphin Inhibitor Composition.

An exorphin-inhibiting composition was created comprising casomorphinase (having DPP IV activity) and gluteomorphinase, and having the following components.

Peptidase FPII, having an activity of 25,000 HUT (hemoglobin units of tyrosine; National Enzyme Company, Forsythe, Mo., USA 65653, and from Valley Research, Inc., South Bend, Ind., USA 46624 as Validase ®FP) and comprising casomorphinase (having DPP IV activity). It was produced by a controlled surface fermentation of *Aspergillus oryzae* on a wheat bran koji culture, followed by extraction with water and then further purification. The peptidase FPII fraction was a white tan, free flowing powder with no offensive odor, had a protease activity of pH 7.0 of NLT 110,000 units/g, a peptidase activity of pH 5.0 of NLT 6,500 units/g, a drying loss of NMT 10%, a condition loss of NMT 10%, heavy metals of NMT 50 PPM, arsenic of NMT 2 PPM, a total plate count of NMT 1,000/g, and was negative for coliforms. The protease activity was determined by a modified Anson-Hajiwara procedure using a Hammerstein casein substrate, while the peptidase activity was determined using synthetic substrate, H-Glu-Tyr-Glu-OH. The Peptidase FPII composition additionally comprised other enzyme activities, including an alkaline protease, a neutral protease, and endoproteases, as well as leucine amino peptidases. Optimum pH was about 6–9 and its stable pH was about 2.8–10.1.

Acid-stable protease ((25 SAPU) Spectrophotometric Acid Protease Units); Bio-Cat, Inc., Troy, Va., USA 22974, and National Enzyme Company, Forsythe, Mo., USA 65653), which is a protease having a higher activity profile at lower pH levels. This component provided continued and additional proteolysis in the acid conditions of the stomach. The enzyme was manufactured with wheat bran culture of Aspergillus and was extracted with water and further purified using ethanol. It was a yellowish powder having an activity of 15,000 units/g wherein one unit of acid protease activity is defined as the quantity of enzyme needed to produce amino acids equivalent to 100 $\mu$mol of tyrosine in 1 ml of filtrate per 60 minutes of 37° C. and pH 3.0.

Protease 20,000 HUT (National Enzyme Company, Forsythe, Mo., USA 65653, and from Valley Research, Inc., South Bend, Ind., USA 46624 as Validase ®FP 600). This enzyme was produced by a controlled fermentation of *Aspergillus oryzae* and contains both endopeptidase and exopeptidase activity. Endopeptidases hydrolyze the interior peptide bonds of protein liberating peptides of varying lengths, and the exopeptidases liberate amino acids by hydrolysis of the peptide bonds at the terminus of the peptide chain. The enzymes have a broad substrate specificity for, e.g., gluten, egg yolk, casein, soya, gelatin, hemoglobin and fish. It has an activity of 500,000 HUT/g, is in a light tan powder and is soluble in water. (One hemoglobin unit on the tyrosine basis (HUT/g) is that activity which produces, in one minute, hydrolysate that has an absorbency at 275 nm equivalent to that of a solution containing 1 $\mu$g/ml of tyrosine in 0.006 N hydrochloric acid.) This component had an optimum pH range of 2.5 to 6.0 30° C.

Lactase, 1,000 ALU (Acid Lactase Units; National Enzyme Company, Forsythe, Mo., USA 65653; Valley Research, Inc., South Bend, Ind., USA 46624). Lactase obtained by a fermentation of *Aspergillus oryzae* and catalyzed the hydrolysis of lactose beta-D-galactoside linkage, liberating one mole of D-glucose and one mole of D-galactose. The component has 100,000 F.C.C. LU (F.C.C. lactase unit)/g, is a light tan amorphous dry powder and is free of offensive odor and taste. 1 F.C.C. LU is that amount of enzyme that will liberate one micromole of o-nitrophenol per minute at pH 4.5 and 37° C. The lactase has an effective pH range of 3.5–6.5 and optimum pH range of 4.5–5.0.

Papain (sulfite free), 2,500,000 F.C.C. PU (Food Chemical Codex Plant Units; National Enzyme Company, Forsythe, Mo., USA 65653). Papain has a relatively broad substrate specificity including substrates containing a bulky non-polar side chain (such as phenylalanine) at the P2 position of a P1–P2 cleavage site.

L-lysine, 100/mg. L-lysine is an amino acid with alkaline properties. It is believed to provide a more alkaline microenvironment for the other enzymes while in the stomach, and thereby tends to increase enzyme activity.

Example 3

Administration of Exorphin-Inhibiting Composition to Human Autism Patients.

The composition of Example 2 was formulated into number 1-size gelatin capsules containing 360 mg of active ingredients plus a rice bran base. The formulation contained no gluten, casein, soy, corn, sugars, flavors, fragrances, preservatives, salicylates, maltodextrin, artificial colors, or other common allergenic substances. One capsule was taken at the beginning of each meal. If the capsules could not be swallowed they could be opened (pulled apart), and the contents added to the first several spoonfuls of food of each meal. The enzyme was not added to all the food or to portions that would not be eaten immediately.

Capsules were taken at the beginning of all meals and snacks (other than drinks: water, juice, colas, etc.). Continual snacking was discouraged as it places a continual demand on the production of digestive enzymes. If the individual forgot to take the capsule at the beginning of a meal, it was taken during or up to 15 minutes after the meal, but the digestive effects were possible lessened in this instance.

The composition was administered to the patients as described above for four weeks.

Example 4

Results of Administration to Human Patients.

The results of the administration in Example 3 indicated that a substantial number of the participants noted significant improvement of their symptoms, as shown in Table 1.

TABLE 1

| Symptom | 0 | 1 | 2 | 3 | 4 | 5 | Blank | ** |
|---|---|---|---|---|---|---|---|---|
| Eye Contact | 17 | 14 | 6 | 2 | 1 | 0 | 3 | 21% |
| Socialization | 12 | 15 | 12 | 1 | 1 | 0 | 2 | 33% |
| Attention | 16 | 15 | 7 | 2 | 1 | 0 | 3 | 23% |
| Mood | 23 | 8 | 6 | 2 | 0 | 0 | 4 | 19% |
| Hyperactivity | 27 | 7 | 1 | 2 | 0 | 0 | 6 | 7% |
| Anxiety | 30 | 5 | 1 | 2 | 0 | 0 | 6 | 7% |
| Stimming | 25 | 5 | 1 | 1 | 1 | 0 | 10 | 7% |
| Comprehension | 11 | 20 | 3 | 3 | 1 | 0 | 6 | 16% |
| Speech | 17 | 13 | 7 | 1 | 2 | 0 | 3 | 23% |
| Sound Sensitivity | 27 | 5 | 1 | 0 | 1 | 0 | 9 | 5% |
| Digestion | 19 | 7 | 5 | 2 | 1 | 0 | 9 | 19% |
| Sleep | 24 | 7 | 2 | 1 | 0 | 0 | 9 | 7% |
| Perseveration | 26 | 4 | 0 | 4 | 0 | 0 | 9 | 9% |

Improvement Ratings:
0 = none
1 = possible
2 = moderate
3 = significant
4 = great
5 = supplied by participant
Blank = no comment on survey
**percentage of group total reporting 2 to 5 improvement rating.

These results indicated that a "dose response" relationship may be present. Such a dose response would reflect that the amount of enzyme was adequate to result in significant changes in some participants, but that such patients would require a higher dose before symptoms were affected. The results also indicated that there may be a certain percentage of children who do not have problems with gluten or casein and use of the composition of Example 2 may assist with bowel function and digestibility of foods but not affect the autism symptoms.

The results also demonstrated that the composition of Example 2 was generally very well tolerated and quite safe. Except for two cases it was noted that adverse responses were generally transient and did not continue throughout the full four weeks. In evaluating the two who experienced these responses, there may have been other factors that could have contributed to some of the symptoms.

In order to determine if a dose relationship may be present, the dosage was increased and again administered to participants, as shown in the following Example 5.

Example 5

Administration Of Exorphin-Inhibiting Composition to Human Autism Patients.

The composition of Example 2 was formulated (as in Example 3) into Number 1-size gelatin capsules containing 360 mg of active ingredients plus a rice bran base. The capsules were administered to patients as described in Example 3, except that two capsules were administered at the beginning of meals. After two weeks, the following results were reported:

TABLE 2

| | Week 1 | | Week 2 | |
|---|---|---|---|---|
| Symptom | $N_1 = 20$ | % | $N_1 = 17$ | %* |
| Eye Contact | 10 | 50 | 11 | 55 |
| Socialization | 11 | 55 | 12 | 60 |
| Attention | 10 | 50 | 8 | 40 |
| Mood | 6 | 30 | 8 | 40 |
| Hyperactivity | 6 | 30 | 4 | 20 |
| Anxiety/Compulsions | 6 | 25 | 6 | 30 |
| Stimming | 3 | 15 | 3 | 15 |
| Speech | 11 | 55 | 9 | 45 |
| Sound Sensitivity | 2 | 10 | 4 | 20 |
| Digestion | 6 | 30 | 3 | 15 |
| Sleep | 5 | 25 | 3 | 15 |
| Perseveration | 4 | 20 | 5 | 25 |
| Individuals not helped at all | 3 | 15 | 2 | 10 |
| Helped moderately or significantly | 9 | 45 | 20 | 50 |

*All % are of $N_1$

From the foregoing, it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. A method of reducing the symptoms of autism in a human patient, comprising orally administering to the patient a composition comprising a physiologically effective amount of a purified casomorphinase which is a dipeptidyl peptidase, and at least one of the group consisting of a physiologically acceptable carrier, an adjuvant, an excipient, a buffer and a diluent, wherein the composition is capable of decreasing the incidence of one or more symptoms consisting of eye contact avoidance, failure to socialize, attention deficit, poor mood, hyperactivity, anxiety, stimming, poor comprehension, inappropriate speech, abnormal sound sensitivity, poor digestion, disrupted sleep, and perseveration, and wherein the decreased incidence is measured relative to the incidence of said one or more symptoms in the untreated individual.

2. The method of claim 1 wherein the dipeptidyl dipeptidase is dipeptidyl peptidase IV.

3. The method of claim 1 wherein the casomorphinase is a purified microbial casomorphinase.

4. The method of claim 3 wherein the casomorphinase is derived from a fungus selected from the group consisting of *Aspergillus oryzae* or *Aspergillus niger*.

* * * * *